United States Patent [19]

Reinehr et al.

[11] Patent Number: 4,670,336
[45] Date of Patent: Jun. 2, 1987

[54] LAUNDRY-STABLE, ANTIMICROBIALLY-ACTIVE FIBERS AND FILAMENTS AND THE PRODUCTION THEREOF

[75] Inventors: Ulrich Reinehr, Dormagen; Karl H. Büchel, Burscheid; Gerhard Jäger, Leverkusen; Manfred Plempel, Haan; Walter Radt, Krefeld, all of Fed. Rep. of Germany

[73] Assignee: Bayer Aktiengesellschaft, Leverkusen, Fed. Rep. of Germany

[21] Appl. No.: 762,659

[22] Filed: Aug. 5, 1985

[30] Foreign Application Priority Data

Aug. 11, 1984 [DE] Fed. Rep. of Germany ....... 3429665

[51] Int. Cl.$^4$ ............................................. D02G 3/00
[52] U.S. Cl. ................... 428/359; 428/361; 428/362; 428/364; 428/368; 428/375; 428/394; 428/907
[58] Field of Search ............... 428/359, 361, 372, 375, 428/364, 394, 362, 907, 369; 8/115.8, 115.6

[56] References Cited

U.S. PATENT DOCUMENTS

| | | |
|---|---|---|
| 3,471,576 | 10/1969 | Klesper et al. ................. 428/907 X |
| 3,852,401 | 12/1974 | Suzuki et al. . |
| 4,185,113 | 1/1980 | Virrion et al. . |
| 4,401,712 | 8/1983 | Morrison ........................ 428/907 X |

FOREIGN PATENT DOCUMENTS 1094258 1/1981 Canada .

*Primary Examiner*—Lorraine T. Kendell
*Attorney, Agent, or Firm*—Sprung Horn Kramer & Woods

[57] ABSTRACT

Fibers and filaments of synthetic polymers containing from 0.1 to 5%, by weight, based on polymer, of an azole compound corresponding to the following general formula:

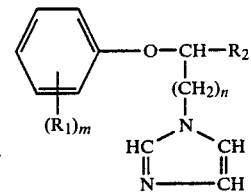

and from 0.1 to 5%, by weight, based on polymer, of a dihydroxydiphenylmethane derivative corresponding to the following general formula:

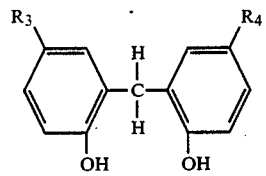

wherein
n represents 0 or 1;
m represents 0, 1 or 2;
$R_1$ represents halogen, halophenyl or phenyl;
$R_2$ represents $-CO-C(CH_3)_3$ or $-CHOH-C(CH_3)_3$; and
$R_3$ and $R_4$ represent halogen,
show laundry-stable, antimicrobial activity.

3 Claims, No Drawings

LAUNDRY-STABLE, ANTIMICROBIALLY-ACTIVE FIBERS AND FILAMENTS AND THE PRODUCTION THEREOF

This invention relates to laundry-stable, antimicrobially-active fibers and filaments and to a process for the production thereof.

Antimicrobially-finished fibers and filaments are to be understood to be fibers and filaments which, by the addition of chemical active substances, develop both antibacterial activity, i.e. activity against bacterial growth, and also antimycotic activity, i.e. acitivity against rotting and fungal attack. Laundry-stable, antimicrobially-active fibers and filaments are fibers and filaments, the antimicrobial activity of which is still present, even after dyeing and repeated washing.

As a result of the application of chemical active substances to the textile material, the substances in question develop the antimicrobial activity thereon under growth conditions for microorganisms by preventing the proliferation or transfer of microorganisms to other articles or organisms.

The antimicrobial finishing of fibers, filaments and textiles is known. In general, the active substances required are applied to the fibers either after of during production. Methods of application to fibers after production include, for example, the application of chemical active substances to piece goods, yarns and combed slivers by the infusion or padding technique.

Known methods of application to fibers during production include the introduction of antimicrobially-active compounds, for example phosphorylated salicylic acid anilides, into the spinning solution of the polymer (DE-OS No. 22 20 907). In this way, the active substance is uniformally distributed over the entire fiber cross-section. Other methods comprise introducing the active substances by copolymerization (DE-OS No. 15 42 945), by microencapsulation (DE-OS No. 22 31 903) or even by introducing an antimicrobial agent into the homogeneous melt of a fiber-forming polymer (DE-OS No. 32 14 610). Another known process for the antimycotic finishing of synthetic fibers produced by melt spinning comprises fixing the active substances to the polymer by adhesion promoters before the spinning process (DE-OS No. 27 10 469).

One disadvantage common to all known methods of applying active substances to fibers and fabrics is that the antimicrobial effect is not laundry-stable. Where the active substances are introduced into the spinning solution of the polymer, particularly during dry spinning, large quantities have to be added to obtain an antimicrobial effect. Most of the active substance is ineffectually bound within the fiber-forming polymer, leaving only the small proportion on the surface of the fiber to develop the antimicrobial effect. However, high concentrations of active substance in the spinning solution also frequently result in serious damage to important fiber properties. Thus, losses of strength, inadequate light and colour stability, streakiness after dyeing, vacuole, natural colour, feel and gloss problems are commonly observed.

Accordingly, an object of the present invention is to provide antimicrobially active synthetic fibers which do not have the above-mentioned disadvantages and, above all, still show high antimicrobial activity after dyeing and washing.

It has now surprisingly been found that this object may be achieved by introducing into synthetic fibers a combination of active substances consisting of a certain azole compound and a certain halogenated phenol compound.

Accordingly, the present invention relates to fibers and filaments of synthetic polymers containing from 0.01 to 5%, by weight, based on polymer, of an azole compound corresponding to the following general formula:

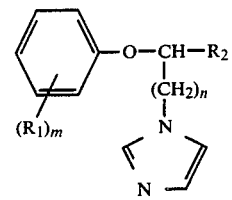

and from 0.01 to 5%, by weight, based on polymer, of a dihydroxydiphenylmethane derivative corresponding to the following general formula:

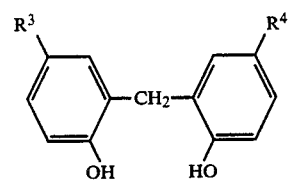

wherein
n represents 0 or 1;
m represents 0, 1 or 2;
$R_1$ represents halogen, halophenyl or phenyl;
$R_2$ represents $-CO-C(CH_3)_3$ or $-CHOH-C(CH_3)_3$; and
$R_3$ and $R_4$ represent halogen.

The fibers and filaments preferably contain from 0.1 to 1%, by weight, of each of the two substances, 1-(4-chlorophenoxy)-1-imidazol-1-yl-3,3-dimethylbutan-2-one and 2,2'-dihydroxy-5,5'-dichlorodiphenylmethane being particularly suitable.

The synthetic fibers in question are polyacrylonitrile fibers containing at least 45%, by weight, of acrylonitrile units, i.e. acrylonitrile homo- and copolymers which may be spun into so-called acrylic or modacrylic fibers, preferably acrylonitrile copolymers containing at least 85%, by weight, of acrylonitrile units.

The filaments and fibers according to the present invention are obtained by introducing the combination of active substances according to the present invention into a spinning solution of the polymer, dry spinning the spinning solution into filaments and then washing, preparing, drying, crimping and, optionally, cutting the thus-spun filaments of fibers and fixing them using saturated steam for at least 3 minutes at at least 120° C. By applying this fixing process, it is surprisingly possible to produce high, dyeing-resistant and laundry-stable antimicrobial activity. Spinning tests have shown that, even in cases where the antimicrobial agents are added to the spinning solution in large quantities amounting, for example, to 5%, by weight, of the azole compound and 5%, by weight, of the halogenated phenol compound (c.f. Example 3), it was not possible to obtain an antimicrobial effect without the saturated-steam fixing step.

Other efforts to obtain antimicrobially-finished dry-spun fibers by various aqueous treatments at boiling temperatures under reflux, under dyeing conditions, at various pH values (c.f. Table 2) or even using short steaming times and at relatively low temperatures (c.f. Table 1), were successful.

In one embodiment of the process according to the present invention, the filaments are brought into contact, after spinning, washing and drawing and before or during antistatic finishing, with a homogeneous emulsion or suspension of the combination of active substances according to the present invention in an aqueous bath at temperatures above 80° C., passed between squeezing rollers and, after fixing in dry heat in the conventional way, are subjected to another contact heat fixing treatment for at least 120 seconds at a surface temperature of at least 200° C.

The filaments are then crimped in the conventional way and optionally cut into staple fibers.

In this embodiment, the spinning process may be a dry or wet spinning process.

Suitable auxiliaries for preparing homogeneous emulsions or suspensions are, for example, polyglycol esters, polyglycol ethers, alkyl ether sulphates and alkyl ether phosphates and also mixtures thereof based on fatty acids, fatty amines and fatty alcohols, such as compounds containing lauryl, stearyl or oleyl groups.

A fatty alcohol-based mixture of equal parts of polyglycol ester, alkyl ether sulphate and alkyl ether phosphate is preferably used.

The preparation of the combination of antimicrobially-active substances in the form of an aqueous, homogeneous suspension is carried out as follows:

The azole compound, 1-(4-chlorophenoxy)-1-imidazol-1-yl-3,3-dimethylbutan-2-one, is melted at up to about 150° C. and the same quantity of the bisphenol derivative of 2,2'-dihydroxy-5,5'dichlorodiphenylmethane is added to the resulting melt. The homogeneous melt formed is introduced with intensive stirring into water heated to approx. 80°-90° C. which contains at least 0.5 g/l of an emulsifier or emulsifier mixture.

The quantities of active substances and additives used are selected in such a way that the homogeneous aqueous suspension contains 12 g/l of azole compound, 12 g/l of bisphenol derivative and 1 g/l of additive. The described suspension is completely homogeneous above 80° C., flocculation and agglomeration occurring at lower temperatures.

The azole derivatives used in accordance with the present invention are known from DE-OS No. 26 00 800.

The bisphenol derivatives are known from Charles C. Yeager, American Dyestuff Reporter 1953, No. 18, pages 591–594 and from H. Klesper, Melliand Textilberichte 1971, No. 5, page 592.

The azole and bisphenol derivatives are best used in equal quantities, by weight. However, they may also be used in different quantities, by weight.

The filaments and fibers produced in accordance with the present invention may be further processed into fabrics under normal conditions in the textile industry. In this connection, the fibers may be processed on their own or in admixture with fibers which have not been antimicrobially-finished. Textiles for which an antimicrobial finish is particularly desirable are, for example, carpets, furniture coverings, bath mats, curtains, tents, tarpaulins, seat cushions, etc. The troublesome fungus and mildew stains, which are formed on awning cloths by the combined effect of heat and moisture after weathering, may also be effectively prevented by the process according to the present invention, i.e. by finishing polyacrylonitrile awning cloths with the present combination of antimicrobial active substances.

Determination of antimicrobial activity

Microbiological tests in the form of the agar diffusion test against three different test germs were carried out on fibers and knitted fabrics antimicrobially-finished in accordance with the present invention.

Agar diffusion test

Quantities of 1 g of the antimicrobially-finished, first undyed and then dyed fibers and test pieces of knitting measuring 2×2 cm (edge length), unwashed and repeatedly washed (10 times), were placed in Petri dishes filled with Nervina agar (composition: 60 g of Nervina malt, 5 g of NaCl, 5 g of peptone, 5 g of glycerin, ad 1 l $H_2O$) in such a way that they were completely covered by the nutrient substrate. The surfaces of the thus-prepared Petri dishes were then uniformaly inoculated with germ suspensions of moulds and bacteria. The moulds were incubated for 7 days at 30° C. and the bacteria for 3 days at 37° C. The moulds used were spore suspensions of *Aspergillus fumigatus* and *Chaetomium globosum*. The test bacterium used was *Staphylococcus aureus* in the form of Standard I nutrient agar (Merck No. 1621). The inhibition zones expected were then measured out and evaluated as follows:

Mark 1: no reduction in growth on the test specimen
Mark 2: up to 25% of the test surface infested
Mark 3: test specimen free from growth
Mark 4: test specimen free, inhibition halo up to 2 mm
Mark 5: test specimen free, inhibition halo >2 mm All the tests were carried out twice, including the growth and nutrient medium checks.

Surface germ count (SGC)

The surface germ count is the number of germs per g of fiber. In the case of an antimicrobial effect, it should be as low as possible. Determination of the SGC was carried out in accordance with DIN 54 378. To this end, the test specimens in the form of fibers were wound onto sterile transparency frames. Quantities of 0.5 g of the fiber material undyed (white), dyed, unwashed and repeatedly washed (10 times) were introduced into Subcuraud glucose/maltose agar (Merck No. 7662) and evaluated after incubation for 5 days at 25° C.

Results

The results of the microbiological tests in the form of the agar diffusion test on fibres and pieces of knitting and of the surface germ counts on fibers are shown in the Tables. In the case of the agar diffusion test, evaluation was carried out on the marking scale defined above and, in the case of the surface germ count, by counting out the number of germs present compared with the starting count. The letter a–d appearing next to the Examples in the Tables have the following meaning:
a=untreated, raw white fibers or knitting
b=raw white fibers or knitting after washing 10 times
c=dyed fibers or knitting
d=dyed fibers or knitting after washing 10 times.

EXAMPLE 1

An acrylonitrile copolymer of 93.6%, by weight, of acrylonitrile, 5.7%, by weight, of methylacrylate and 0.7%, by weight of sodium methallyl sulphonate, K-value 81 (Fikentscher, Cellulose-Chemie, 13, (1932), page 58) was converted, by stirring and heating to 80° C. for 1 hour with dimethyl formamide, into a spinning solution having a solids content of 30%, by weight, to which 0.1%, by weight, of 1-(4-chlorophenoxy)-1-imidazol-1-yl-3,3-dimethylbutan-2-one and 0.1%, by weight, of 2,2'-dihydroxy-5,5'-dichlorodiphenylmethane, based in each case on polymer solids, were added. The spinning solution was then filtered and dry spun from a 240-bore spinneret at a take-up rate of 350 m/min. The spun material, which had an overall denier of 2280 dtex, was collected on bobbins and combined to form an after-treatment tow having an overall denier of 1,140,000 dtex. The tow was washed in water heated to 80° C. and then drawn in a ratio of 1:3.6 in boiling water. The two was then antistatically finished and dried at 160° C. in a drum dryer in which it was allowed to shrink by 20%. The tow was then crimped, cut into 60 mm staple fibers and fixed using saturated steam for 5 minutes at 120° C. in a screen belt steamer. The ratio of fiber throughput to the quantity of saturated steam used was 1:1. The staple fibers were then blown dry and delivered to a bale press. The individual fibers had a final denier of 3.3 dtex. Some of the antimicrobially-finished fibers were then dyed using a blue dye corresponding to the following formula:

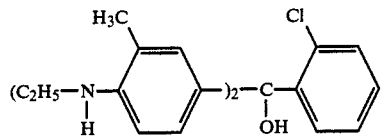

Both the raw white and alo the blue-dyed antimicrobially-finished fibers were then spun into three-cylinder yarns of dtex 276×1 (count 36/1) from which a fabric knitted in so-called "Milano Rib" was produced. The knitted fabrics were then washed 10 times using 5 g/l of a commercial, domestic 30° C. detergent (pre-wash and main wash cycles, 30° C. program, liquor ratio 1:30). The fabrics were rinsed three times per wash and tumble-dried at 60° C. between each wash. The results of microbiological testing in the form of the agar diffusion test on fibers and pieces of knitting are shown in the following Table. Evaluation was carried out on the marking scale defined above.

TABLE 1

| Origin | Treatment | Inhibiting effect against moulds | | Bacteria |
|---|---|---|---|---|
| | | Aspergillus fumigatus | Chaetomium globosum | Staphylococcus aureus |
| Fibre | a | 5 | 5 | 5 |
| | b | 4 | 4 | 5 |
| | c | 5 | 5 | 5 |
| | d | 4 | 4 | 4 |
| Knitting | a | 5 | 5 | 5 |
| | b | 4 | 4 | 4 |
| | c | 5 | 5 | 5 |
| | d | 3 | 4 | 4 |

EXAMPLE 2

An acrylonitrile copolymer was dissolved as in Example 1 and, following the addition of 0.5%, by weight, of 1-(4-chlorophenoxy)-1-imidazol-1-yl-3,3-dimethylbutan-2-one and 0.5%, by weight, of 2,2'-dihydroxy-5,5'-dichlorodiphenylmethane, was spun into filaments and after-treated to form fibers having a final individual denier of 3.3 dtex. Some of the fibers were again dyed blue. The raw white fibers and dyed fibers were made up into pieces of knitting, washed 10 times in a domestic washing machine and then microbiologically tested. The results are shown in Table 2.

TABLE 2

| Origin | Treatment | Inhibiting effect against moulds | | Bacteria |
|---|---|---|---|---|
| | | Aspergillus fumigatus | Chaetomium globosum | Staphylococcus aureus |
| Fibre and knitting | a | 5 | 5 | 5 |
| | b | 5 | 5 | 5 |
| | c | 5 | 5 | 5 |
| | d | 5 | 5 | 5 |

As may be seen from Example 2, excellent antimicrobial activity was obtained for the antimicrobially-finished fibers and pieces of knitting in the raw white, dyed and repeatedly washed state.

Table 3 below shows the antimicrobial activity of fibers produced in the same way as in Example 2, but using different steaming treatments.

TABLE 3

| No. | Steaming temperature °C. | Steaming time mins. | Inhibiting effect against moulds | | Bacteria Staphylococcus aureus |
|---|---|---|---|---|---|
| | | | Aspergillus fumigatus | Chaetomium globosum | |
| 1 | 105 | 1 | 1 | 1 | 1 |
| 2 | " | 3 | 1 | 1 | 2 |
| 3 | " | 5 | 2 | 1-2 | 2 |
| 4 | 110 | 1 | 1 | 1 | 1 |
| 5 | " | 3 | 1-2 | 2 | 2 |
| 6 | " | 5 | 2 | 2 | 2 |
| 7 | 120 | 1 | 1 | 1 | 1-2 |
| 8 | " | 2 | 2 | 2 | 2-3 |
| 9 | " | 3 | 3 | 3 | 4 |
| 10 | " | 4 | 4 | 4 | 5 |
| 11 | 130 | 1 | 4 | 4 | 5 |
| 12 | " | 3 | 5 | 5 | 5 |

Table 4 shows the antimicrobial activity of fibers produced in the same way as in Example 2, but without the steaming treatment, for various aqueous treatments. For blank dyeing, the treatment was carried out below boiling temperature at a pH of from 4 to 5. The dyeing tests were carried out as follows: 5 g of napped fibers were refluxed for 1 and 2 hours in a flask filled with 1 liter of dye liquor. After dyeing, the dye was still present in excess. The dyed fibers were then rinsed in running water, thoroughly boiled in water for 30 minutes and dried at 50° C. The dye liquor contained 1 g/l of the blue dye according to the Example 1 and was adjusted to a pH of approx. 4 using approx. 0.2–0.5 ml/l of glacial acetic acid.

TABLE 4

| No. | Aqueous treatment | Inhibiting effect against moulds | | Bacteria Staphylococcus aureus |
|---|---|---|---|---|
| | | Aspergillus fumigatus | Chaetomium globosum | |
| 1 | boiling water/1 h | 1 | 1 | 1 |
| 2 | boiling water/ 2 h | 1 | 1 | 1 |
| 3 | boiling water/10 h | 2 | 1-2 | 2 |
| 4 | blank dyeing 1 h | 1 | 1 | 1 |
| 5 | blank dyeing 2 h | 1 | 1-2 | 1-2 |
| 6 | dyeing test 1 h | 1 | 1 | 1 |
| 7 | dyeing test 2 h | 1-2 | 1 | 1-2 |

As may be seen from Table 3, a steaming temperature of at least 120° C. coupled with a residence time of at least 3 minutes, but preferably 5 minutes, is required for the adequate antimicrobial-finishing of acrylic fibers which have been produced by dry spinning and in which the abovementioned antimicrobially-active combination of an azole derivative and a bisphenol derivative are incorporated during spinning. Table 4 shows that aqueous boiling treatments, even at different pH values, do not produce adequate antimicrobial activity.

EXAMPLE 3

(Comparison)

An acrylonitrile copolymer according to Example 1 was dissolved in the same way as in that Example and, following the addition of 5%, by weight, of 1-(4-chlorophenoxy)-1-imidazol-1-yl-3,3-dimethylbutan-2-one and 5%, by weight, of 2,2-dihydroxy-5,5'-dichlorodiphenylmethane, was converted into a spinning solution having a solids content of 30%, by weight. The spinning solution was then filtered and spun in the same way as in Example 1. The spun material was collected on bobbins, doubled and aftertreated without steaming to form fibers having a final denier of 3.3 dtex. Some of the fibers were again dyed. Both the raw white and the dyed antimicrobially-finished fibers were then spun into three-cylinder yarns of dtex 288×1 (count 36/1) from which fabrics were knitted in Milano Rib. The knitted fabrics were washed 10 times in a domestic washing machine. The fibers and knitted fabrics, both raw white and dyed, were then microbiologically tested by the agar diffusion test using the same moulds and bacteria as in Example 1. In every case, evaluation produced the mark 1, i.e. there was no reduction in the growth of the test germs on the fibers and knitted fabrics.

EXAMPLE 4

An acrylonitrile copolymer of 93.6%, by weight, of acrylonitrile, 5.7%, by weight, of methylacrylate and 0.7%, by weight, of sodium methallyl sulphonate, K-value 81, was converted, by heating to 80° C. with dimethyl formamide, into a spinning solution having a solids content of 30%, by weight, which was filtered and dry spun from a 240-bore spinneret at a take-up rate of 350 m/minute. The spun material, which had an overall denier of 2280 dtex, was collected on bobbins and doubled to form a tow having an overall denier of 684,000 dtex. The tow was washed in water heated to 80° C. and then drawn in a ratio of 1:3.6 in boiling water. The tow was then passed through a treatment bath steam heated to 90° C. which contained 12 g/l of 1-(4-chlorophenoxy)-1-imidazol-1-yl-3,3-dimethylbutan-2-one, 12 g/l of 2,2'-dihydroxy-5,5'-dichlorodiphenylmethane and 1 g/l of a fatty alcohol-based additive consisting of equal parts of a polyglycol ester, alkyl ether sulphate and alkyl ether phosphate. The residence time in the treatment bath was approx. 3 seconds. After squeezing between a pair of pressure rollers, the tow was coated in an aqueous bath with 10 g/l of an antistatic preparation and fixed with dry heat at 170° C. for 1.5 mins. in a tumble dryer in which it was allowed to shrink by 20%. The tow was then repeatedly looped around 6 heating godets on which it was subjected to contact heat fixing at a surface temperature of 200° C. The residence time of the tow on the heating godets was 120 seconds. The tow was then crimped and cut into 60 mm staple fibers. The individual fibers had a final denier of 3.3 dtex. Some of the antimicrobially-finished fibers were then dyed using a blue dye corresponding to the formula in Example 1. Both the raw white and also the dyed antimicrobially-finished fibers were then spun into three-cylinder yarns of dtex 278×1 (count 36/1) from which a fabric was knitted in Milano Rib. The knitted fabrics were then washed 10 times with 5 g/l of a commercial, domestic 30° C. detergent (pre-wash and main wash cycles, 30° C. program, liquor ratio 1:30). The fabrics were rinsed three times per wash and tumble-dried at 60° C. after each wash. The active substance content before and after 10× washing of the raw white and dyed materials was determined by analysis of the antimicrobially-finished knitted fabrics. The individual active substance contents are shown in the following table:

| Active substance | Active substance contents on Milano Rib fabric (%, by weight) | | | |
| --- | --- | --- | --- | --- |
| | before washing | | after washing 10 times | |
| | raw white | dyed | raw white | dyed |
| Azole compound | 0.255 | 0.223 | 0.218 | 0.204 |
| Bisphenol compound | 0.313 | 0.280 | 0.273 | 0.246 |

The active substance content of the antimicrobially-finished knitted fabrics was determined as follows:

10 g of knitted fabric were dissolved at room temperature in 400 ml of 50% by weight aqueous sodium thiocyanate solution. Working in the absence of oxygen, the active substances were extracted from that solution with ether, separated up by thin-layer chromatography using gradient elution on silica gel and quantitatively determined by densitometric UV-measurement of the chromatograms.

More examples of the production of antimicrobial fibers are shown in Table 5 below. In every case, the starting fibers had a denier of 3.3 dtex. Variations were made in the contents of active substances (azole and bisphenol compound) and in the surface temperature and residence time of the contact heat fixing treatment on the heating godets. All fibers were washed 10 times, the washing machine being filled with a 1 kg load including filling material. Once again, the contents of active substances were analytically determined on the raw white and washed (10×) antimicrobially-finished fibers.

TABLE 5

| Example No. | Surface temperature heating godets °C. | Residence time on the heating godets seconds | Active substance contents (%, by weight) | | | |
| --- | --- | --- | --- | --- | --- | --- |
| | | | azole compound | | bisphenol compound | |
| | | | before washing | after washing 10 times | before washing | after washing 10 times |
| 5 | 180 | 60 | 0.244 | 0.001 | 0.213 | 0.001 |
| 6 | " | 120 | 0.222 | 0.001 | 0.241 | 0.005 |
| 7 | 200 | 30 | 0.271 | 0.006 | 0.273 | 0.008 |
| 8 | " | 60 | 0.252 | 0.012 | 0.311 | 0.016 |
| 9 | " | 120 | 0.241 | 0.218 | 0.301 | 0.264 |
| 10 | " | 180 | 0.101 | 0.091 | 0.142 | 0.123 |

TABLE 5-continued

| Example No. | Surface temperature heating godets °C. | Residence time on the heating godets seconds | Active substance contents (%, by weight) azole compound | | bisphenol compound | |
|---|---|---|---|---|---|---|
| | | | before washing | after washing 10 times | before washing | after washing 10 times |
| 11 | 220 | 90 | 0.026 | 0.022 | 0.029 | 0.027 |
| 12 | " | " | 0.052 | 0.043 | 0.055 | 0.044 |
| 13 | " | " | 0.109 | 0.091 | 0.124 | 0.108 |

As may be seen from Table 5, there is always a distinct loss of active substances from the fibers unless the fibers are adequately fixed. Firm anchorage of the active substance combination to the fiber walls requires contact heat fixing for at least 120 seconds at a surface temperature of 200° C. (cf. Example 9).

After washing 10 times, the contents of active substances (azole and bisphenol compound) in the fiber walls are generally several percent below the quantity originally applied. This is attributable to the diffusion of the active substances from the fiber walls to the fiber surface as a result of repeated washing and is also desirable for the permanent development of antimicrobial activity.

EXAMPLE 14

After the washing and drawing step, part of the tow of Example 4 was again passed through a steam-heated treatment bath containing the concentrations of active substances and additives mentioned in Example 4. In addition, the bath contained 10 g/l of an antistatic preparation. The bath temperature was from 92° to 95° C. and the residence time approx. 2.5 seconds. The tow was again squeezed between a pair of pressure rollers and after-treated in the same way as in Example 4. Analysis of the active substance contents on untreated, dyed and washed (10×) fibers produced the following results:

| Active substance | Active substance contents on fibers (%, by weight) | | | |
|---|---|---|---|---|
| | before washing | | after washing 10 times | |
| | raw white | dyed | raw white | dyed |
| Azole compound | 0.241 | 0.222 | 0.201 | 0.200 |
| Bisphenol compound | 0.308 | 0.279 | 0.272 | 0.249 |

EXAMPLE 15

An acrylonitrile copolymer having the chemical composition indicated in Example 1 was converted, by heating to 80° C. with dimethyl formamide, into a 30%, by weight, spinning solution which was filtered and then dry spun from a 360-bore spinneret. A filtered 10%, by weight, stock solution of an acrylonitrile copolymer containing 10%, by weight, of an organic orange pigment is dispersed form was introduced in a sidestream ahead of the spinneret. The take-up rate was 400 m/min. The spun material, which had an overall denier of 2630 dtex, was collected on bobbins and doubled to form a tow having an overall denier of 789,000 dtex. The tow was washed in water heated to 80° C. and then drawn in a ratio of 1:6.0 in boiling water. The tow was then treated with an emulsifier-containing active substance combination for about 2 seconds at a bath temperature of from 90° to 95° C., coated with antistatic preparation and further processed into fibers having a final denier of 1.3 dtex and a staple length of 40 mm.

The orange pigmented, antimicrobially-finished fibers were then spun into yarns (count 40/1) from which a 230 g/m² "wevenit" fabric was produced. The wevenit fabric was washed 10 times in a domestic washing maching in the same way as in Example 1. The active substance content was then determined by comparison with an unwashed wevenit fabric. The active substance contents are shown in the following Table:

| Active substance | Active substance contents on wevenit fabric (%, by weight) | |
|---|---|---|
| | before washing | after washing 10 times |
| Azole compound | 0.291 | 0.264 |
| Bisphenol compound | 0.320 | 0.288 |

EXAMPLE 16

An acrylonitrile copolymer having the chemical composition indicated in Example 4 was converted, by heating to 80° C. with dimethyl formamide, into a spinning solution having a solids content of 22%, by weight, which was then filtered and wet-spun from a 300-bore spinneret. The precipitation bath consisted of 45%, by weight, of dimethyl formamide and 55% by weight, of water. The precipitation temperature was 56° C. The take-up rate was 5 m/minute. The spun material, denier 2940 dtex, was collected on bobbins and doubled to form a tow having an overall denier of 102,900 dtex. The tow was then drawn in a ratio of 1:5.5 in boiling water, washed and passed for 3 seconds through a steam-heated treatment bath heated to 95° C. which contained 12 g/l of azole compound, 12 g/l of bisphenol derivative and 1 g/l of an emulsifier-containing additive according to Example 1. After squeezing between a pair of pressure rollers, the tow was coated with 10 g/l of an antistatic preparation in an aqueous bath and then cut into 60 mm stable fibers (denier 2.2 dtex). Some of the antimicrobially-finished fibers were again dyed using the blue dye according to Example 1. The raw white and dyed fibers were spun into three-cyclinder yarns from which fabrics were knitted in Milano Rib. The knitted fabrics were washed 10 times in a domestic washing machine and analyzed for the active substance contents.

| Active substance | Active substance content on knitted fabric (%, by weight) | | | |
|---|---|---|---|---|
| | before washing | | after washing 10 times | |
| | raw white | dyed | raw white | dyed |
| Azole compound | 0.22 | 0.191 | 0.290 | 0.244 |
| Bisphenol compound | 0.214 | 0.163 | 0.243 | 0.201 |

Tables 6 to 8 below show the antimicrobial activities.

TABLE 6

Agar diffusion tests of antimicrobially finished fibers

| Fibers produced in accordance with Example No. | Inhibiting effect against moulds | | | | Bacteria |
|---|---|---|---|---|---|
| | Aspergillus fumigatus | Aspergillus niger | Chaetomium globosum | Trichoderma viride | Staphylococcus aureus |
| 4 a | 5 | 5 | 5 | 5 | 5 |
| b | 5 | 5 | 5 | 5 | 5 |
| c | 5 | 5 | 5 | 5 | 5 |
| d | 5 | 5 | 5 | 5 | 5 |
| 5 a | 5 | 5 | 5 | 5 | 5 |
| b | 1 | 1 | 1 | 1 | 1 |
| 6 a | 5 | 5 | 5 | 5 | 5 |
| b | 1 | 1 | 1 | 1 | 1 |
| 7 a | 5 | 5 | 5 | 5 | 5 |
| b | 2 | 2 | 1 | 1 | 2 |
| 8 a | 5 | 5 | 5 | 5 | 5 |
| b | 3 | 3 | 3 | 5 | 4 |
| 9 a | 5 | 5 | 5 | 5 | 5 |
| b | 5 | 5 | 5 | 5 | 5 |
| 10 a | 5 | 5 | 5 | 5 | 5 |
| b | 5 | 5 | 5 | 5 | 5 |
| 11 a | 5 | 5 | 5 | 5 | 5 |
| b | 5 | 5 | 5 | 5 | 5 |
| 12 a | 5 | 5 | 5 | 5 | 5 |
| b | 5 | 5 | 5 | 5 | 5 |
| 13 a | 5 | 5 | 5 | 5 | 5 |
| b | 5 | 5 | 5 | 5 | 5 |
| 14 a | 5 | 5 | 5 | 5 | 5 |
| b | 5 | 5 | 5 | 5 | 5 |
| c | 5 | 5 | 5 | 5 | 5 |
| d | 5 | 5 | 5 | 5 | 5 |
| 15 c | 5 | 5 | 5 | 5 | 5 |
| d | 5 | 5 | 5 | 5 | 5 |
| 16 a | 5 | 5 | 5 | 5 | 5 |
| b | 5 | 5 | 5 | 5 | 5 |
| c | 5 | 5 | 5 | 5 | 5 |
| d | 5 | 5 | 5 | 5 | 5 |

TABLE 7

Agar diffusion tests of antimicrobially-finished knitted fabrics

| Knitted fabrics produced in accordance with Example No. | Inhibiting effect against moulds | | | | Bacteria |
|---|---|---|---|---|---|
| | Aspergillus fumigatus | Aspergillus niger | Chaetomium globosum | Trichoderma viride | staphylococcus aureus |
| 4 a | 5 | 5 | 5 | 5 | 5 |
| b | 5 | 5 | 5 | 5 | 5 |
| c | 5 | 5 | 5 | 5 | 5 |
| d | 5 | 5 | 5 | 5 | 5 |
| 15 c | 5 | 5 | 5 | 5 | 5 |
| d | 5 | 5 | 5 | 5 | 5 |
| 16 a | 5 | 5 | 5 | 5 | 5 |
| b | 5 | 5 | 5 | 5 | 5 |
| c | 5 | 5 | 5 | 5 | 5 |
| d | 5 | 5 | 5 | 5 | 5 |

TABLE 8

Surface germ counts of antimicrobially-finished fibers

| Fibers produced in accordance with Example No. | Surface germ count |
|---|---|
| 4 a | 3 |
| b | 0 |
| c | 3 |
| d | 0 |
| 14 a | 3 |
| b | 0 |
| c | 2 |
| d | 0 |
| 15 c | 2 |
| d | 0 |
| 16 a | 1 |
| b | 0 |
| c | 1 |
| d | 0 |

According to these tests results, the fibers and knitted fabrics finished in accordance with the present invention are fully effective and may be described as permanently antimicrobially-finished. As may also be seen from Tables 6 to 8, active substance contents of only about 0.01%, by weight, based on PAN solids, both of azole derivative and of bisphenol derivative are sufficient to produce effective antimicrobial activity (cf. Example 8).

We claim:

1. Fibers and filaments of synthetic acrylic polymers having a combination of antimicrobial agents incorporated therein and firmly anchored to the walls thereof said combination consisting of from 0.1 to 5%, by weight, based on polymer, of an azole compound corresponding to the following general formula:

and from 0.1 to 5%, by weight, based on polymer, of a dihydroxydiphenylmethane derivative corresponding to the following general formula:

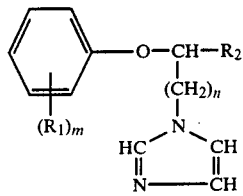

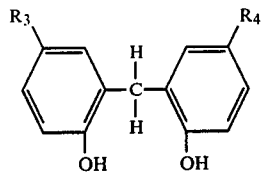

wherein
n represents 0 or 1;
m represents 0, 1 or 2
$R_1$ represents halogen, halophenyl or phenyl;
$R_2$ represents $-CO-C(CH_3)_3$ or $-CHOH-C(CH_3)_3$; and
$R_3$ and $R_4$ represents halogen.

2. Fibers and filaments according to claim 1, wherein the azole compound is 1-(4-chlorophenoxy)-1-imidazol-1-yl-3,3-dimethylbutan-2-one and the dihydroxydiphenyl methane derivative is 2,2'-dihydroxy-5,5'-dichlorodiphenylmethane.

3. Fibers and filaments as claimed in claim 1, wherein the synthetic polymer is polyacrylonitrile containing at least 45%, by weight, of acrylonitrile units.

* * * * *